United States Patent
Xue et al.

(10) Patent No.: US 6,645,488 B2
(45) Date of Patent: Nov. 11, 2003

(54) MICROENCAPSULATED PHEOCHROMOCYTE OF OX ADRENAL MEDULLA AS MEDICINE FOR CURING PAIN

(76) Inventors: Yilong Xue, Institute of Basic Medical Science, 28# Fuxing Road, Beijing 100853 (CN); Limin He, Institute of Basic Medical Science, 28# Fuxing Road, Beijing 100853 (CN); Zhengfu Wang, Institute of Basic Medical Science, 28# Fuxing Road, Beijing 100853 (CN); Li Zhang, Institute of Basic Medical Science, 28# Fuxing Road, Beijing 100853 (CN); Xinjian Li, Institute of Basic Medical Science, 28# Fuxing Road, Beijing 100853 (CN)

(*) Notice: Subject to any disclaimer, the term of this patent is extended or adjusted under 35 U.S.C. 154(b) by 98 days.

(21) Appl. No.: 10/017,159

(22) Filed: Dec. 14, 2001

(65) Prior Publication Data

US 2002/0119125 A1 Aug. 29, 2002

Related U.S. Application Data

(63) Continuation of application No. PCT/CN00/00155, filed on Jun. 14, 2000.

(30) Foreign Application Priority Data

Jun. 16, 1999 (CN) ......................................... 99109057 A

(51) Int. Cl.$^7$ .................................................. C12N 5/00
(52) U.S. Cl. ..................................... 424/93.7; 424/489
(58) Field of Search ................................. 424/93.7, 489

(56) References Cited

U.S. PATENT DOCUMENTS

| 5,182,111 A | * | 1/1993 | Aebischer et al. | 424/424 |
| 5,585,183 A | | 12/1996 | Chu | 428/402.2 |
| 5,730,974 A | | 3/1998 | Sagen | 424/93.7 |
| 5,762,925 A | | 6/1998 | Sagen | 424/93.7 |
| 5,766,907 A | | 6/1998 | Chang et al. | 435/178 |
| 5,876,742 A | | 3/1999 | Cochrum et al. | 424/424 |

* cited by examiner

*Primary Examiner*—Jean C. Witz
(74) *Attorney, Agent, or Firm*—Ladas & Parry

(57) ABSTRACT

Microencapsulated medicine of ox adrenal medulla pheochromocyte (BBC) for treating pain is prepared through the following steps: 1. suspending BBC in solution of sodium alginate; 2. dispersing the suspension in solution of calcium chloride to form calcium alginate bead deposit; 3. mixing the deposit with solution of polylysine to form a coating and depositing; 4. mixing the deposit with sodium alginate to form a coating; 5. displacing the calcium ions in deposit with sodium citrate for microencapsulating BBC; 6. transferring the microencapsulated BBC into culture liquid for storage. The medicine can release analgesic substance for several months after it be implanted into human body.

3 Claims, No Drawings

MICROENCAPSULATED PHEOCHROMOCYTE OF OX ADRENAL MEDULLA AS MEDICINE FOR CURING PAIN

This application is a continuation of PCT/CN00/00155, filed Jun. 14, 2000.

TECHNICAL FIELD

The present invention relates to the animal cell medicine, specifically to a microencapsulated medicine of ox adrenal medulla pheochromocyte (BCC) for treating pain.

BACKGROUND ART

Pain is a common symptom caused by several disease factors and causing serious soreness to patients. Although current medicines, such as morphine-like, can bring analgesic effects in short-term, its repeating administration usually result in drug-resistance and habituation. As adrenal medulla pheochromocyte can secrete certain substance in association with analgesic effects, such as methionine enkephalin(MEK), leucineenkephalin (LENK) and monamine substances, so once pheochromocyte had been implanted into subarachnoid space of spinal of human or animal, it can act as a "mini bio-pump" and release analgesic substances continuously in a long period, and wouldn't result in drug-resistance and habituation. So in the beginning of 1980's, two research groups from USA and Switzerland tried to implant homogenous (human, rat) adrenal medulla tissues and chromaffin cells into subarchnoid space of spinal cord for treating pain and had finally obtained satisfactory results. Because of the less sources of human adrenal medulla tissues and chromaffin cells, in 1990's, the research group from USA had tried to implant heterogeneous ox adrena medulla pheochromocyte (hereafter abbreviated as BCC) into subarachnoid space of spinal cord of cancer patients to cure pain. In order to overcome the immuneexclusion reaction, they used polyacrylamide hollow fiber tube of 5 cm in length and 1 mm in diameter to coat BCC. As the said hollow fiber tube only allow small molecules to pass through, the secreta of BCC can diffused slowly and uniformly from the fiber tube to perform the analgesic effect, while macromolecular immunoglobulin in host body can't pass through the hole of tube wall, so that the cells can survive in host body in a long period(about 1 year) and allows continuous delivery of analgesic substances to relief the pain of patients. But the hollow fiber tube has a large volume. On one side, the dead volume of tube affect the dispersion of nutrients and metabolites, which make the cells inside tube can't survive chronically. On the other hand, implantation of fiber tube with large volume into subarachnoid space of spinal cord would stimulate and oppress spinoneure, thereby cause many undesirable side effects. Moreover, as the volume of hollow fiber tube is large, it must to be implanted into subarachnoid space by surgical operation, which would injure patient more or less. In the meantime, the hollow fiber tube made of materials such as chitosan, polyacrylamide and carboxymethyl cellulose (used in USA) have poor tissue biocompatibility, which cause tissue reaction in host body. On the other side, the microcapsules with three layer membrane structure of sodium alginatepolylysine-sodium alginate (APA microcapsule) have little volume (200–1000 $\mu$m in diameter) and high biocompatibility, which contribute that microcapsule survive chronically and well in host cell and the cells inside microcapsule survive chronically. The experiments have indicated that microcapsule membrane can cut off macromolecule with molecular weight beyond 110,000 Kd (dalton), prevent immunoglobulin and immunological competence cell pass through the said membrane into microcapsule to destroy inside animal cell, which thus provide proper immunity protection. Experiments also indicated that APA microcapsules have proper biocompatibility, and have long term existence (about one year and half) in small or big animal body. The research on implantation of islands of Langerhans, liver cells, parathyroid and genetic recombinant growth-hormone secretory cells for treating disease model animal have provided the evidence that the said APA microcapsule protect heterogeneous implant from host immune system. However, so far, there is no report about using APA microencapsulated pheochromocyte of ox adrenal medulla as medicine for curing pain.

DESCRIPTION OF THE INVENTION

The object of the present invention is to provide APA microencapsulated medicine of ox adrenal medulla pheochromocyte for curing pain, which have advantages of proper biocompatibility, long acting time, lower side effect and can operate easily.

The present inventor has conducted deep research based on aforementioned existing technique, found that employing following embodiment can arrive at said aims, thus accomplish the present invention.

Embodiment of the present invention described as follows:

1. Microencapsulated medicine of ox adrenal medulla pheochromocyte for treating pain, which is prepared through the following steps:
   (1) mixing the ox adrenal medulla pheochromocyte with 10–20 g/L solution of sodium alginate to form suspension, the said suspension contains $0.1-1 \times 10^{10}$ cells per liter.
   (2) dispersing the suspension of step (1) into 80–120 mmol/L calcium chloride solution or calcium lactate solution, in the form of microdrop of diameter of 150–1000 $\mu$m by spray device, the proportion of the two solution is to let 1 liter mixture contains $0.1-1 \times 10^8$ cells, setting 5–20 minutes, removing the supernatant after depositing completely, obtaining the calcium alginate bead deposit which contains ox adrenal medulla pheochromocyte;
   (3) adding the deposit derived from step (2) into the 0.3–0.7 g/L polylysine solution, the proportion of the two solution is to let 1 liter mixture contains $0.2-2 \times 10^8$ cells, mixing it uniformly, setting 5–20 minutes, removing the supernatant after deposit completely, getting the deposit;
   (4) adding the deposit derived from step (3) into the 1.0–2.0 g/L sodium alginate solution, the proportion of the two solution is to let 1 liter mixture contains $0.2-2 \times 10^8$ cells, mixing it uniformly, setting 3–15 minutes, removing the supernatant after deposit completely, getting the deposit;
   (5) adding the deposit derived from step (4) into 40–70 mmol/L sodium citrate solution, the proportion of the two solution is to let 1 liter mixture contains $0.2-2 \times 10^8$ cells, mixing it uniformly, setting 5–20 minutes, removing the supernatant after deposit completely, obtaining the microencapsulated medicine of ox adrenal medulla pheochromocyte deposit;
   (6) washing the deposit derived from step (5) by adding it into the 9 g/L sodium chloride solution, finally transferring the deposit into a cell culture, and storing it as microencapsulated medicine of ox adrenal medulla pheochromocyte.

2. The microencapsulated medicine of ox adrenal medulla pheochromocyte in item 1, wherein the said ox adrenal medulla pheochromocyte has a purity of at least 80%.

3. The microencapsulated medicine of ox adrenal medulla pheochromocyte in item 1, which is characterized in that in said step (2) dispersing the suspension derived from step (1) in microdrop state with a diameter of 180–500 μm.

As for use, the APA-microencapsulated BCC ($2\sim9\times10^6$ cells) was injected into subarachnoid space of spinal cord of patients (e.g. cancer patient), which would cause analgesic effect within 4–24 hours and the effect could last for over 9 months by each injection.

The detailed explanation of embodiments of the invention is described as following.

Within the forementioned several embodiments, the 1st item is essential characteristic, and that 2nd and 3rd are preferred.

The said ox adrenal medulla pheochromocyte (BCC) of present invention refers to the ox adrenal medulla cells capable of being dyed with dye containing chromium, which can secrete monamine, enkephalin (including monamine enkephalin (MEK), leucineenkephalin) and neurotrophy factors et al, these substances have analgesic effect.

The methods of acquiring BCC and its purification methods belong to conventional technology. For example, make ox adrenal react with collagenase to decompose collagen tissue, then seperate ox adrenal tissue into single cell by mechanical method, then filter by filter screen of 170 mesh (88 μm), ox adrenal medulla cell (which contains pheochromocyte, endotheliocyte, mechanocyte and blood cells) pass through the filter screen centrifuge the fluid under the screen and remove supernatant, thus acquire the aforesaid ox adrenal medulla cell sediment, in which the pheochromocyte is about 50~60% of total cells, both endotheliocyte and mechanocyte are about 40~50% of total cells, since the shape of blood cell is small, so it usually can't be counted in the total cells. Notably, as the BCC is about 50~60% of ox adrenal medulla cell, so which can be applied to the present invention without being purified. However, in order to improve the curing effect, it is preferably purified to a purity of 80%. The purification methods, for example, conventional wall-attaching purification method which is based on the distinct attachment tendency of different cells can be used. For example, culture mixture which contains pheochromocyte, endotheliocyte, fibroblast and blood cells are cultured in culture-flask for hours, most of fibroblasts attach the wall, while pheochromocytes, endotheliocytes and blood cells don't attach to wall, thus most fibroblasts can be removed through changing bottle. For the blood cells can't grow on wall, so most of blood cells can be removed through culturing them for longer time (for example 24–28 hours) and changing bottles again after the pheochromocytes and endotheliocytes being attached to wall. After changing bottle 2 times, the purity of BCC can arrive at 80% of total cells (except the blood-cell). As for the methods of cell counting, conventional counting process of observing under microscope after dyed can be used. Such as "Trypan blue stain", see "Tissue Culture Media and Reagents", page 1566.

In the six steps of essential technology characteristics in the present invention, the said liquid amount of each step is determined according to the confined cells number. For example, 1 liter suspension derived from step (1) of embodiment 1 contains $0.1\times10^{10}$ cells, while 1 liter mixture liquid from step (2) contain $0.1\times10^8$ cells, that is to say, cell concentration of suspension from step (1) is about 100 times of that from step (2), thus, it preferably disperse 1 ml suspension from step (1) into 100 ml calcium chloride solution of step (2), and the like.

The aim of forming calcium alginate bead in step (2) is to create a condition for gaining microcapsules containing ox adrenal medulla pheochromocyte in step (5). In step (5), sodium ion of sodium citrate replace the calcium ion of calcium alginate bead to form many microcapsules with small hole. Those microcapsules contain a great deal of BCC, and BCC encapsulated by sodium alginate.

There has no specific limit to the methods of forming calcium alginate bead, it only required that the sodium alginate suspension containing BCC can disperse into the solution of calcium chloride in adequately tiny liquid-drop. The diameter of said microdrop of suspension of sodium alginate is usually in the scope of 150–1000 μm, preferably in the scope of 180–500 μm. If micro-drop diameter is more than 1000 μm, the said acquired microcapsules is too large so that it burst easily when being injected into animal or human body, that isn't expected. Liquid-drop scatter methods usually include pinhead injection method, nebulization and so on, and nebulization is preferred, the most preferred method is to spray by electrostatic droplet generator manufactured by Toronto University, Canada (see SUN, A.M. Micro-encapsulation of pancreatic islet cell: a bio-artificial endocrine pancreas In methods in Enzymology, Vol. 137, page 575–580, 1988).

The embodiments of the present invention have been explained. After reading them and the following examples, the skill in art can comprehend the present invention easily.

Compared to the similar technology in the art, the present invention have following positive effects:

The animal experiment indicated that to inject the microcapsule containing $0.2\sim1\times10^5$ BCC cells into subarachnoid space of spinal cord of normal rat through APA microencapsulated animal cell medicine (microcapsule diameter is 150~1000 μm) can rise heat-pain threshold value (by conventional uplift-foot test and swing-tail test to detect the rat's response to acute nocuity hot stimulation) obviously (rised 80~110%), action time last over 9 months. Clinical trials provided the evidence that implantation of microencapsulated BCC ($2\sim9\times10^6$ cells) into subarachnoid space of spinal cord of cancer patient can relief the pain within 4~24 hours, wherein most of patients no more need to use other analgesic medicines. The pain score value (graded by two doctors according to international VAS grading method) descend obviously, spirit and appetite conditions have an improvement, therapeutic effect has last over 120 days, and it has no obvious side effect. The fact indicated that implantation of APA microencapsulated BCC can provide obvious analgesic effect, and APA microcapsule can protect implant (BCC) from being destroyed by host immune system, thus the microencapsulated BCC can survive chronically in heterogeneous animal body and act lasting analgesic effect.

The present invention have following advantages comparing to current technologies:

1. APA microcapsules according to the present invention have a small volume, which thus have at least three advantages, (1) it accelerate scattering of nutrients and metabolites, the intracapsular cells can survive chronically; (2) it is not necessary to implant hollow fiber tube with operation, but to inject microcapsules into subarachnoid space of spinal cord only by ordinary waist-penetratting method, thus it have tiny damage to tissue; (3) it usually not readily stimulate and oppress spinal cord nerve in subarachnoid space of spinal cord;

2. Compared to immune isolation membranes made of other material, APA microcapsules have proper biocompatibility;
3. Lots of experiments have indicated that APA microcapsules of the present invention have good immunity protection.
4. The BCC can secrete analgesic substances continually (last over 3 months) in host body to act sustaining analgesic effect, thus it resolved the undulatory analgesic effect resulted by clinical administration;
5. Microencapsulated BCC can act sustaining analgesic effect in host body, that avoid drug resistance and habituation conferred by repeatly using of analgesic;
6. Compared to human adrenal medulla pheochromocyte, the ox adrenal medulla pheochromocyte can be gained in gross;
7. Low temperature technology can be adopted to conserve microencapsulated BCC, which contributes to long-range transport and volume production.

In summary, the present invention has the characteristics of outstanding effect for treating pain, long acting time, safely use, convenient operation, stable quality, volume production and short production cycle. Which have wide foreground in clinic.

Optimum Embodiment of the Present Invention

The following examples, experiments and application examples further explain the present invention, but they can't be construed as limitation of the invention.

EXAMPLE 1

Isolation and Purification of BCC

1. Take 12 fresh bovine adrenal (ischemic time less than 1 hour at room temperature) from shambles, carry back to laboratory in cold storage condition quickly for preparation.
2. Inject 1 g/L collagenase I solution into adrenal vein, 5 ml collagenase I solution per adrenal, then setting 30 minutes at 37° C., in order to make the collagenase and colloid around the bovine adrenal cells react sufficiently.
3. slit the cortex along vertical axis of adrenal, isolate the medulla and snip it into pieces.
4. Add the 60 ml 1 g/L collagenase I solution into medulla derived from step 3, setting 30 minutes.
5. filter by steel screen of 170 mesh (88 $\mu$m), collecting the liquid under the screen.
6. centrifuge the fluid under the screen and remove supernatant, and acquire the sediment (including BCC, endotheliocytes, fibroblasts and blood cells) containing ox adrenal medulla cells.
7. count with trypan blue stain method, the total cell (except the blood cells) is $5.8 \times 10^7$, and the survival rate is 90%.
8. transfer the cells into two culture bottle, add 20 ml DMEM (Dulbeco's Modified Eagle Medium)nutrient solution(which contain 100 unit/ml penicillin, 100 $\mu$g/ml streptomycin, bovine serum 10 vol %) into each bottle. Culture it in the culture-box containing 5 vol $CO_2$ at 37° C., five hours later, change the bottle, keep on culture to make most BCC attach bottle wall, stand-by application.

Usually culture should continue at least 24 hours. When preparing microencapsulated animal cell medicine, we only need to remove the solution in culture bottle and collect the BCC from culture bottle by using conventional trypsin digest method for further operation.

Notable, the method of Example 1 belongs to routine technique, which has no limit on the present invention.

EXAMPLE 2

Preparation of Microencapsulated Animal Cell Medicine 1. centrifugalize the BCC according to the method of Example 1 to acquire BCC sediment, wash with normal saline and dilute it to 1 ml, then transfer it into centrifuge tube.
2. count with trypan blue stain method, the total cells (beside the blood cells) are $3 \times 10^6$, and the survival rate is 82%.
3. add 1 ml 15 g/L sodium alginate solution to form suspension by stir.
4. spray the suspension into 100 ml of 100 mmol/L calcium chloride solution by electrostatic droplet generator (made by Toronto University, Canada), ten minutes later obtain calcium alginate bead deposit containing cells and the deposit bead diameter within 180~500 $\mu$m, then remove the supernatant after deposit completely.
5. add the calcium alginate bead into 50 ml of 0.5 g/L polylysine solution, mix uniformly, set 10 minutes at room temperature, remove the supernatant after deposit completely.
6. add the deposit derived from step 5 into 60 ml of 1.5 g/L sodium alginate solution, mix uniformly, set 10 minutes at room temperature, remove the supernatant after deposit completely.
7. add the deposit derived from step 5 into the 60 ml 55 mmol/L sodium citrate solution, mix uniformly, set 10 minutes at room temperature, remove the supernatant after deposit completely, and obtain the microencapsulated animal cell medicine containing BCC.
8. wash deposit with 9 g/L sodium chloride solution, then transfer the said deposit into DMEM nutrient solution according to step 8 of Example 1 for culture, which as microencapsulated BCC medicine for injection application.

Experimental Example 1

Effect of Microencapsulated BCC on Rat Pain Threshold

1. Ten Wister rats were enrolled in the experiment, each rat weights 300±30 g.
2. deposit the microencapsulated BCC suspension derived from example 2,wash three times with 9 g/l sodium chloride solution, and obtain sodium chloride suspension. Inject the suspension into subarachnoid space of spinal cord of ten rats, $1 \times 10^5$ BCC/20 $\mu$l sodium chloride solution per rat, the result indicated that heat-pain threshold value (by conventional uplift-foot test and swing-tail test to detect the rat's response to acute nocuity hot stimulation) of all rats being injected microencapsulated BCC rise obviously (increased 80~110% than before being injected), action time last over 9 months.

Experimental Example 2

Usage of Microencapsulated BCC in Treating Cancer Patients

Suspend the APA microencapsulated BCC (about $7 \times 10^6$ cells) into 5 ml sodium chloride solution with the concentration of 9 g/L, and inject it into subarachnoid space of spinal cord of cancer patient who must be administrated analgesic chronically by conventional lumbar puncture method. Ten patients with cancer pain were assessed for degree of pain (VAS method),the results suggest that scores of pain (VAS method) of nine patients were decreased from the average of 6~10 degree to 0~2 degree; 4 of 9 patients were able to discontinue analgesics at the day when being transplanted, the other five patients discontinue analgesic from the second or third day after the transplantation. Without using any immunsuppressants, analgesic time of one patient last over 120 days, the other 6 patients last over 70 days. The 9 patients have euphoria and incremental sappetite during the treating. Only 1 patient of the total 10 patients requires to being administrated analgesic sequentially, but reduce the half dosage. No obvious toxin and side effects be observed in the 10 patients.

Specific Embodiments (1) Patient 1, male, 42 years old, suffered from non-Hodgkin's lymphoma. He had to administrate 60 mg meshcontin per day before the microencapsulated BCC $7 \times 10^6$ cells transplantation was carried out, and he was able to discontinue analgesics from being administrated 4 hours later, and his VAS was decreased from 8 to 0, the effect has continued for more than 120 days.

(2) Patient 2, female, 45 years old, suffered from Hodgkin's lymphoma. She had to administrate 300 mg fenbid per day before the microencapsulated BCC $7.5 \times 10^6$ cells transplantation was carried out, and she was able to discontinue analgesics from being administrated 18 hours later, and her VAS was decreased from 6 to 0, the effect has continued for more than 90 days.

(3) Patient 3, female, 47 years old, suffered from metastatic mammary carcinoma in bone. She had to administrate 60 mg meshcontin and 300 mg fenbid per day before the microencapsulated BCC $7 \times 10^6$ cells transplantation was carried out, and she only administrated 150 mg fenbid per day after being administrated 24 hours later, 3 days later, no any analgesics was required for her, and her VAS was decreased from 10 to 1, the effect has continued for more than 80 days.

(4) Patient 4, female, 56 years old, suffered from metastatic lung carcinoma in bone. She had to administrate 60 mg meshcontin per day before the microencapsulated BCC $7 \times 10^6$ cells transplantation was carried out, and she only administrated 30 mg meshcontin per day after being administrated 24 hours later, 6 days later, no any analgesics was required for her, and her VAS was decreased from 10 to 2, the effect has continued for more than 80 days.

(5) Patient 5, female, 60-years old, suffered from osteoma multiplex. She had to administrate 20 mg morphina per day before the microencapsulated BCC $7 \times 10^6$ cells transplantation was carried out, and she only administrated 10 mg morphina per day after being administrated 24 hours later, 6 days later, no any analgesics was required for her, and her VAS was decreased from 10 to 1, the effect has continued for more than 60 days.

The statistics of effect for treating pain as follows:

So far, 22 patients with cancer pain were enrolled in this treating, 21 patients of them have good analgesic effect, total efficiency is 95%. According to the one analgesic time, analgesic time of 3 patients last over 300 days, the longest duration was more than 570 days, most of them over 100 days.

Further, the treating for 2 patients with refractory neurodynia also have fine analgesic effect.

INDUSTRY APPLICATION

Microencapsulated ox adrenal medulla pheochromocyte medicine of the present invention have small volume (180~500 μm in diameter), which can be easily implanted into the subarachnoid space of spinal cord, the cells inside microcapsule can survive chronically in the human body and have long-term analgesic effect, and it has no side effect caused by stimulation and oppress. Moreover, the said microencapsulated cells can be prepared in large batches and were convenient for long distance transportation.

What is claimed is:

1. A microencapsulated medicine of ox adrenal medulla pheochromocyte for treating pain, which is prepared through the following steps:

(1) mixing the ox adrenal medulla pheochromocyte with 10–20 g/L solution of sodium alginate to form suspension, which contains $0.1-1 \times 10^{10}$ cells per liter said suspension, (2) dispersing the suspension of step (1) into 80–120 mmol/L calcium chloride solution or calcium lactate solution in the state of microdrops of diameter of 150–1000 μm by spray device, the proportion of the two solution is to ensure 1 liter mixture to contain $0.1-1 \times 10^8$ cells, setting 5–20 minutes, removing the supernatant after depositing completely, then obtaining the calcium alginate bead deposit which contains ox adrenal medulla pheochromocytes;

(3) adding the deposit derived from step (2) into the 0.3–0.7 g/L polylysine solution, the proportion of the two solution is to ensure 1 liter mixture contains $0.2-2 \times 10^8$ cells, mixing uniformly, setting 5–20 minutes, removing the supernatant after depositing completely, getting the deposit;

(4) adding the deposit obtained from step (3) into 1.0–2.0 g/L sodium alginate solution, the proportion of the two solution is to ensure 1 liter mixture contains $0.2-2 \times 10^8$ cells, mixing it uniformly, setting 3–15 minutes, removing the supernatant after depositing completely, getting the deposit;

(5) adding the deposit obtained from step (4) into 40–70 mmol/L sodium citrate solution, the proportion of the two solution is to ensure 1 liter mixture contains $0.2-2 \times 10^8$ cells, mixing it uniformly, setting 5–20 minutes, removing the supernatant after depositing completely, getting the microencapsulated pheochromocyte deposit of ox adrenal medulla;

(6) washing the deposit obtained from step (5) by adding it into the 9 g/L soludium chloride solution, finally transferring the deposit into a cell culture, and storing it as microencapsulated medicine of ox adrenal medulla pheochromocyte.

2. A microencapsulated medicine of ox adrenal medulla pheochromocyte of claim 1, which is characterized in that the said ox adrenal medulla pheochromocyte has a purity of at least 80%.

3. A microencapsulated medicine of ox adrenal medulla pheochromocyte of claim 1, which is characterized in that in said step (2) dispersing the suspension obtained from step (1) in microdrop state of diameter of 180–500 μm.

* * * * *